United States Patent [19]

Hausfeld

[11] 4,401,538
[45] Aug. 30, 1983

[54] ISOELECTRIC FOCUSING TECHNIQUES AND DEVICES

[76] Inventor: A. David Hausfeld, 1833 S. Ocean Dr., Hallandale, Fla. 33009

[21] Appl. No.: 269,478

[22] Filed: Jun. 2, 1981

[51] Int. Cl.³ .............................................. C23C 15/00
[52] U.S. Cl. ............................ 204/180 P; 204/299 R; 204/301
[58] Field of Search ................ 204/180 P, 299 R, 301

[56] References Cited

U.S. PATENT DOCUMENTS

| | | | |
|---|---|---|---|
| 3,655,541 | 4/1972 | Strickler | 204/180 R |
| 4,148,703 | 4/1979 | Trop et al. | 204/180 P |
| 4,204,929 | 5/1980 | Bier | 204/301 |
| 4,217,193 | 8/1980 | Rilbe | 204/180 P |
| 4,234,400 | 11/1980 | Kaplan et al. | 204/299 R |
| 4,289,596 | 9/1981 | Satoh | 204/299 R |
| 4,310,407 | 1/1982 | Kaneko et al. | 204/299 R |

*Primary Examiner*—Arthur P. Demers
*Attorney, Agent, or Firm*—Schiller & Pandiscio

[57] ABSTRACT

An isoelectric focusing technique and apparatus employ an isoelectric focusing channel in which: (1) at least a portion of the channel wall extending between the anode and cathode compartments is constructed in such a way that electric lines of force pass through this portion while nevertheless a substantial component of the field is parallel the channel wall; and (2) this portion is selectively permeable to the ions of the electrolyte.

12 Claims, 8 Drawing Figures

ISOELECTRIC FOCUSING TECHNIQUES AND DEVICES

BACKGROUND OF THE INVENTION

This invention relates to electrokinetic methods of separating mixtures of various substances, and more particularly to the method known as isoelectric focusing used in the separation of mixtures of amphoteric substances. Specifically, the present invention relates to the method of and apparatus for establishing stable pH gradients in isoelectric focusing.

Amphoteric substances are substances that can behave either as acids or as bases, depending upon the hydrogen ion concentration of the solution in which they are present. At low pH values, amphoteric substances tend to acquire net positive charges, while at high pH values, they tend to acquire net negative charges. At an intermediate pH value (which varies from substance to substance), amphoteric substances exhibit net zero charges, and are then said to be at their isoelectric points.

Proteins are an example of naturally occuring amphoteric molecules. In addition to amphoteric molecules, mixtures of larger particles, such as viruses, cells, and cell organelles also exhibit an amphoteric character. In particular, various components of blood, e.g., the several kinds of white blood cells, are amphoteric. It is therefore very useful to have methods of separating mixtures of amphoteric substances, as such methods may be useful as analytical tools in biochemical investigations, in clinical medicine as an aid in the diagnosis of disease, and as technique useful in the preparation of quantities of purified substances, such as the insulins, the interferons, and the like.

Isoelectric focusing is a recently introduced method of separating mixtures of amphoteric substances. (For example, see "Isoelectric Focusing", P. G. Righetti and J. W. Drysdale, *Laboratory Techniques in Biochemistry and Molecular Biology*, T. S. Work and E. Work, editors, North Holland Publishing Company, Amsterdam, 1976, vol. 5, p. 335, and "Isoelectric Focusing and Isotachophoresis", N. Catsimpoolas, editor, *Annals of the New York Academy of Sciences*, June 15, 1973, vol. 209.) Isoelectric focusing may be described briefly as follows: a solution containing a mixture of amphoteric substances to be separated is placed in a channel along which a pH gradient has been established, and along which an electric field is applied by appropriate anode and cathode means. The pH gradient is usually established such that the pH value increases in the direction from anode to cathode. Under the influence of the electric field, particles having a net positive charge will migrate in the direction of the cathode while particles having a net negative charge will migrate in the direction of the anode. Neutral particles will experience no migration due to the field. Thus, under the influence of both an electric field and a pH gradient, amphoteric particles will separate, with each species of particle migrating to and concentrating at that position along the channel that has the pH value corresponding to the isoelectric point of the particular particle.

A number of methods have been used to establish a pH gradient in isoelectric focusing apparatus. A common prior art method involves the use of a mixture of amphoteric molecules of low molecular weight known as carrier ampholytes. The carrier ampholytes employed in the mixture are selected to have their isoelectric points at different pH values and to have optimum buffering capacity at these values. When placed in a channel under the influence of an electric field, a solution of carrier ampholytes will come to a steady state in which the several kinds of molecules will be stacked along the channel according to their isoelectric points, thus establishing a pH gradient.

There are several disadvantages associated with this method of establishing a pH gradient. Firstly, a phenomenon known as cathodic drift occurs. Briefly, the steady state positions of the various carrier ampholyte molecules drift slowly in the direction of the cathode. Consequently, the positions to which the amphoteric molecules being assayed or separated also slowly drift in the direction of the cathode. To achieve good separation, a sufficient time interval must be allowed from the start of the process to permit the various amphoteric molecules in an initially homogeneous mixture to migrate to the pH zones corresponding to their various isoelectric points. However, it will be appreciated that cathodic drift of the carrier ampholyte (and the pH zones) tends to mix the already separated molecules. Thus, cathodic drift limits both the yield and the resolving power of the separation method.

In addition, to separate amphoteric molecules with only slightly different isoelectric points, it is advantageous to have a shallow pH gradient (i.e., a gradient over a small pH interval). However, the smallest practicable interval that may be achieved with carrier ampholytes is on the order of 0.5 pH units.

Another disadvantage associated with the use of carrier ampholytes arises because certain amphoteric molecules form complexes with the carrier ampholytes. These complexes are focused according to the isoelectric points of the complexes. Thus, a single molecular species may be focused at several different positions along the channel depending upon the number of different molecules of the carrier ampholyte with which it forms complexes. This complicates both analytical and preparatory uses of isoelectric focusing.

Additionally, if isoelectric focusing is to be used for the preparation of purified substances, the carrier ampholytes will have to be removed in a subsequent operation. As it may be of primary importance that these substances remain biologically active, it is desirable to keep the number of operations necessary for the purification process to a minimum. Therefore it is desirable to achieve the pH gradient without carrier ampholytes.

In addition, it is difficult to separate molecules of the carrier ampholytes from certain low molecular weight amphoteric species such as the short polypeptides, which represent an important class of compounds of biological interest. It is also difficult to distinguish between the carrier ampholytes and the short polypeptides with the usual analytical methods of staining and spectral analysis. Again it is therefore desirable to achieve the pH gradient without carrier ampholytes.

Further, carrier ampholytes are relatively expensive.

Previous methods have been proposed in which isoelectric focusing is performed without carrier ampholytes. One such method involves dividing the focusing channel into several compartments held at graded pH values. The compartments are separated by membranes that allow the passage of the mixture to be separated yet maintain the selected pH values. (See, for example, A. J. P. Martin and F. Hampson, *Journal of Chromatography*, volume 159, 1978, p. 101.) A disadvantage of this approach is that membranes so constructed as to allow the passage of large molecules and particles, as many of the amphoteric substances of interest are, usually produce electroendosmotic flows that tend to disrupt the pH gradient. An additional disadvantage of this technique is that the pH gradient so established is not a continuous function, but, rather, a series of discrete values. Thus, a large number of compartments are required to obtain the resolutions required for most analytical purposes, a consideration which severely limits such applications of this type of isoelectric focusing device.

Still other methods use the principle of steady state electrolysis of buffer solutions in conjunction with two equal and oppositely-directed fluid flows between anode and cathode compartments. Focusing occurs in a convection-free zone, typically a flowtight gel, powder paste, or the like, between the cathode and anode and separate from the flow streams. (See, for example, H. Rilbe, *Journal of Chromatography*, volume 159, 1978, p. 193, and U.S. Pat. No. 4,217,193.) It is particularly difficult with this method to maintain stable concentration gradients, especially in the presence of anti-convective media.

OBJECTS OF THE INVENTION

It is therefore a general object of the present invention to provide an improved method for establishing a pH gradient for use in isoelectric focusing.

More specifically, it is an object of the present invention to provide a pH gradient that does not drift.

Still another object of the present invention is to provide a pH gradient over an interval significantly less than 0.5 pH units.

Yet another object of the present invention is to provide a method of establishing a ph gradient without the use of carrier ampholytes.

It is also an object of the present invention to provide a pH gradient which does not require compartmentation of the focusing channel by a large number of membranes.

BRIEF DESCRIPTION OF THE INVENTION

These and other objects are met by the present invention of an isoelectric focusing technique and apparatus which in a preferred embodiment employs an isoelectric focusing channel provided with the following two interdependent features:

(1) at least a portion of a bounding surface of the focusing channel running between anode means and cathode means is constructed in such a way that electric lines of force pass through it while nevertheless a substantial component of the field is parallel to the surface; and (2) this surface portion is designed to be selectively permeable to the ions of the electrolyte.

In a preferred embodiment, the selectively permeable wall section is a thin ion-selective membrane selected to be permeable to the anions of the electrolyte, which for the pH range of 4.5 to 5 is preferably a buffer solution of acetic acid and sodium acetate in water. This membrane separates a pair of parallel channels, both of which communicate between an anode and a cathode means. One of the channels is an ancillary channel, and is configured to have a variable cross-section, preferably monotonically increasing from anode to cathode. The other channel is the focusing channel, and preferably is of constant cross-section, smaller than the smallest cross-section of the auxiliary channel. The conductivity of the ion-selective membrane is of the order of magnitude of the conductivity of the electrolyte. Consequently, the electric lines of force between the anode and cathode means in the pair of channels will become less dense as the cross-section of the variable channel increases, crossing the membrane. As the membrane is relatively impermeable to them, the cations in the focusing channel are confined to move along that channel under the influence of the electric field in the channel. This field monotonically increases from the cathode to anode means. Consequently, a cation concentration gradient is produced along the focusing channel. An equilibrating concentration of anions effectively establishes a corresponding pH gradient, the permeability of the membrane to anions allowing anions such as the acetate ion to cross into the focusing channel from the ancillary channel as necessary.

It will be appreciated that, with a given electrolyte and anode to cathode potential, the pH at any point along the channel is dependent primarily on the decreasing density of the electric lines of force, i.e., on the geometry of the channels. Consequently, zones of constant pH will not drift. Further, the geometry of the channel may be so chosen as to produce virtually any pH gradient (including a variable gradient) desired. Additionally, it should be noted that this approach for establishing a pH gradient does not rely on carrier ampholytes, nor on polyacrylamide gels, nor does it approximate such a gradient by a series of discrete pH values.

Other objects of the invention will in part be obvious and will in part appear hereinafter. The invention accordingly comprises the apparatus possessing the construction, combination of elements, and arrangement of parts and the method involving the several steps and the order and relation of one or more of such steps with respect to each of the others which are exemplified in the following detailed disclosure and the scope of the application all of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

In the various views, like index numbers refer to like parts.

DETAILED DESCRIPTION OF THE INVENTION

Figure 1:
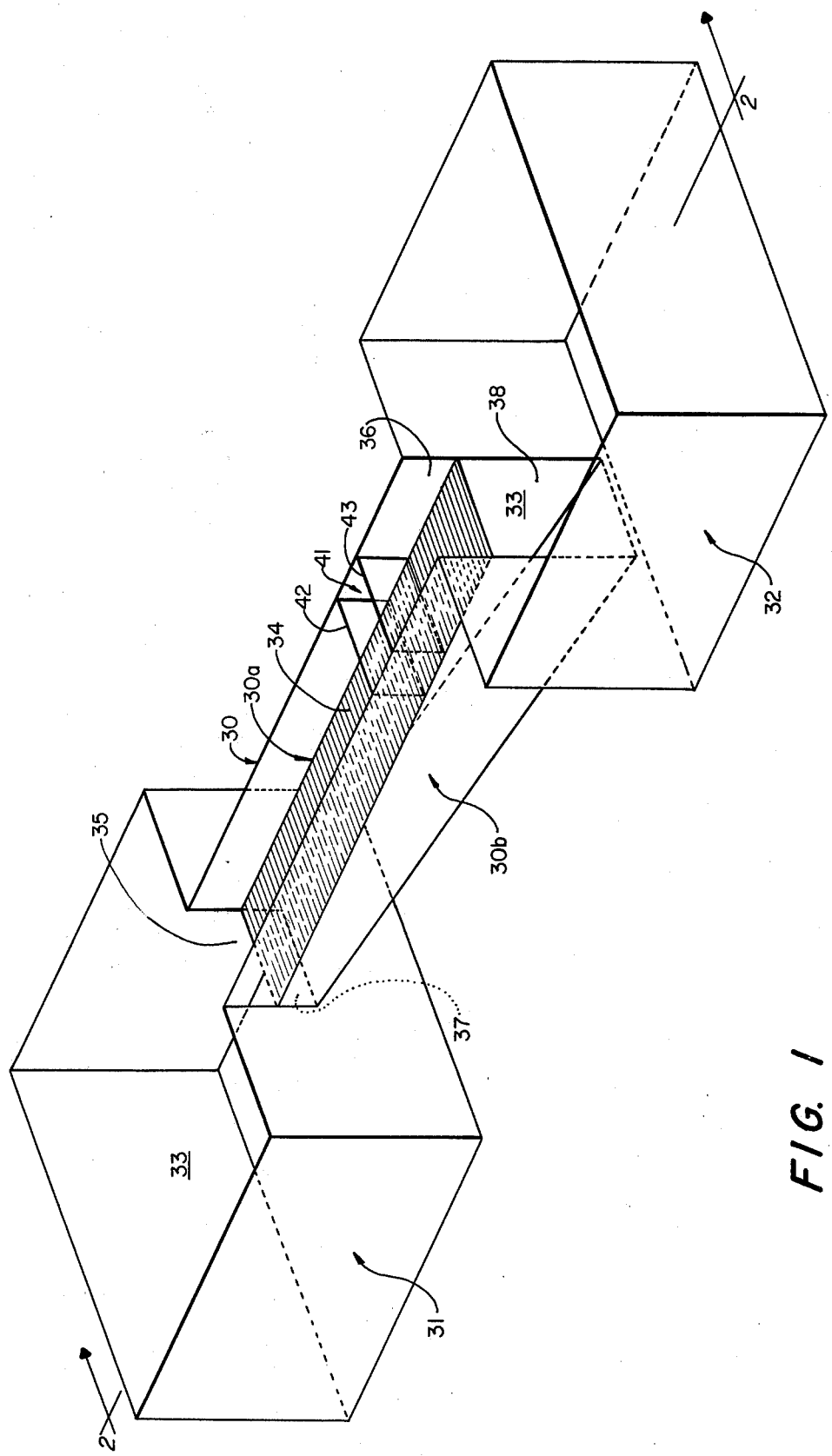
FIG. 1 is a schematic representation, in perspective seen from above, or a preferred embodiment of the present invention, with the top removed to show internal structure.

Referring to FIG. 1, there may be seen a preferred embodiment of the present invention comprising conduit 30, connecting and communicating with anode and cathode electrolyte chambers 31 and 32, respectively. Anode electrolyte chamber 31, cathode electrolyte chamber 32, and conduit 30 are filled with electrolytic solution 33, which in a preferred embodiment is a solution of acetic acid and sodium acetate in water, although it will be understood other electrolytes may be used. Anode electrode means and cathode electrode means (not shown) are provided respectively in anode electrolyte chamber 31 and cathode electrolyte chamber 32. As is well known by those skilled in the art, these electrode means may comprise conducting materials such as platinum or graphite connected to suitable electrical power supplies and in contact with the respective electrolyte solutions. Additionally, as is also well known, certain components of the electrolyte may be prevented from coming into contact with the electrode materials by suitably surrounding the electrode materials with ion-selective membranes. As will be understood by those skilled in the art, the structure delimiting conduit 30 and chambers 31 and 32 is of a material such as glass, chosen to be both impermeable to and non-reactive with electrolytic solution 33 and also substantially electrically non-conductive.

In a preferred embodiment, conduit 30 is in the form of an open-ended tapering hollow conduit of rectangular transverse cross-section, its smallest end being attached to and communicating with the interior of cathode electrolyte chamber 31. Conduit 30 is bifurcated into focusing channel 30a and ancillary channel 30b by selectively permeable membrane 34. Selectively permeable membrane 34 is bound to the walls of conduit 30 such that, within the conduit channels 30a and 30b may directly communicate with one another only through the membrane, although both channels communicate with both anode and cathode chambers 31 and 32. Selectively permeable membrane 34 is in the form of a rectangular sheet, and is so disposed as to provide focusing channel 30a with a substantially constant transverse cross-section while providing ancillary channel 30b with a variable transverse cross-section. In the embodiment of FIG. 1, the cross-sectional area of ancillary channel 30b is everywhere substantially larger than the cross-sectional area of channel 30a. For example, channel 30a may be in the form of a shallow rectangular channel 0.5 millimeter deep while ancillary channel 30b may be in the form of a rectangular trough of variable depth within a range of several centimeters.

Selectively permeable membrane 34 is chosen to be selectively permeable to selected ions of the electrolyte. For the purposes of the present invention, a bounding surface of the focusing channel may be considered to be selectively permeable if, for given electric fields on both sides of the surface (i.e., inside and outside the focusing channel) the ratios of the mobilities within the selectively permeable material to that in the channel (i.e., the ratios of the drift velocities in the direction of the electric field per unit electric field within the membrane and in the free electrolyte) of selected different ions of the electrolyte are significantly different. (For a further discussion of membranes and in particular anion and cation selective membranes, see "Principles of Electrodialysis," J. L. Eisenmann, et al., in *Physical Methods of Chemistry*, A. Weissberger and B. W. Rossiter (editors), John Wiley and Sons, New York, 1971, Vol. 1, part 2B, p. 367). In the embodiment under discussion, membrane 34 is fabricated from an anion selective membrane sheet of the type commonly used in electrodialysis, such as anion membrane sheet number 103-PZL-386 manufactured by Ionics, Inc., of Watertown, Mass. It will be understood, however, that different membranes might be employed. Preferably the membrane is one which will support a very low level of electroendosmotic flow.

Focusing channel 30a communicates with anode chamber 31 through aperture 35, and with cathode chamber 31 through aperture 36. Apertures 35 and 36 are of the same size as the (constant) transverse cross-section of channel 30a. Ancillary channel 30b communicates with anode chamber 31 through aperture 37 and with cathode chamber 32 via aperture 38. In the particular embodiment of FIG. 1, the cross-section of ancillary channel 30b increases from anode chamber 31 (and aperture 37) to cathode chamber 32 (and aperture 38), and apertures 37 and 38 are respectively dimensioned to match the smallest and the largest of the ancillary channel's transverse cross-sections.

As will be described, this arrangement permits a steady state ion concentration gradient to be maintained within focusing channel 30a, the gradient increasing or decreasing from anode to cathode. In particular, a hydrogen ion concentration gradient may be established, thereby effecting a pH gradient. A mixture of amphoteric molecules may therefore be introduced into focusing channel 30a and subjected to isoelectric focusing. As will be understood by those skilled in the art, the maintenance of a steady state ion concentration gradient within focusing channel 30a may require the maintenance of constant ion concentrations in anode and cathode electrolyte chambers 31 and 32 respectively. This may be accomplished with methods well known in the art, such as incorporating a circulation system (not shown) to provide a constant flow of electrolyte through each electrolyte chamber, or, alternatively, dimensioning the anode and cathode chambers such that the volume of electrolyte solution 33 in each chamber is substantially larger than the volume of electrolyte solution within the channel. It is particularly advantageous to have identical electrolyte solutions flowing through both anode and cathode electrolyte chambers. As is well known, this may be easily accomplished by providing a single reservoir with suitable stirring means and pumping means so that electrolyte solution may be pumped in a continuously circulating path between reservoir and anode and cathode electrolyte chambers. The anolyte (an acid in the pH-gradient case) produced in the anode electrolyte chamber may then be neutralized by the catholyte (a base) produced in the cathode electrolyte chamber when both solutions are mixed in the single reservoir. This arrangement may then require only the addition of water to the reservoir during isoelectric focusing.

Figure 2:
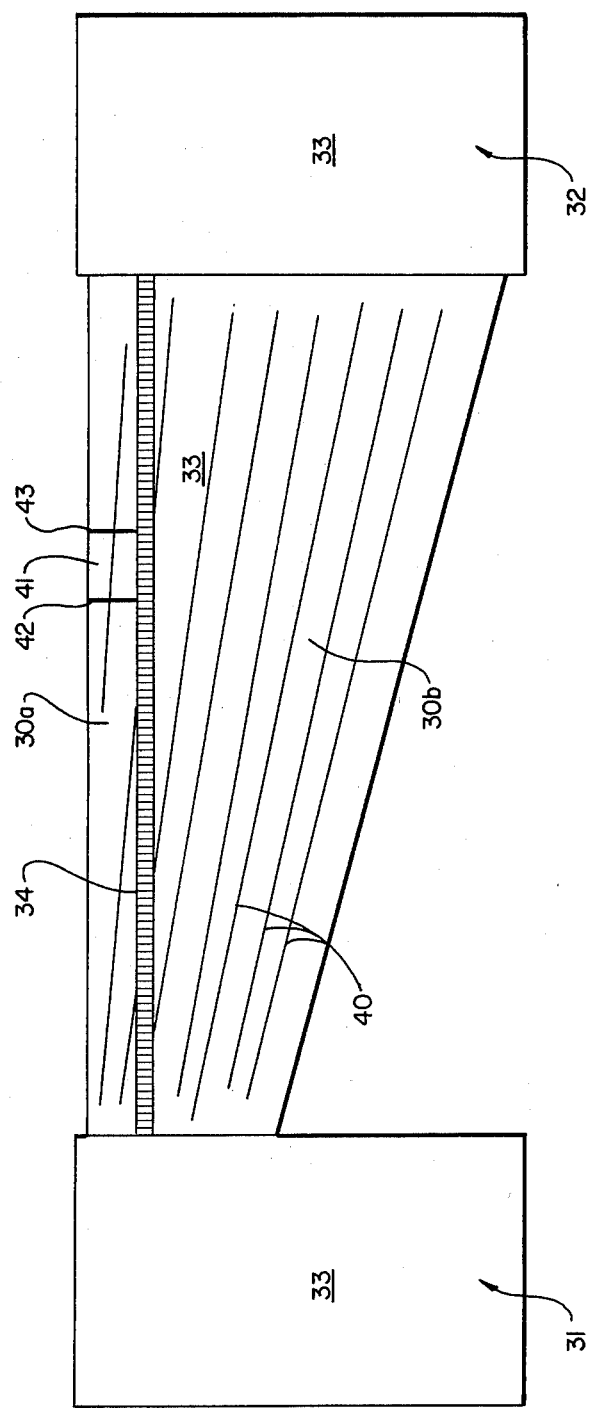
FIG. 2 is a schematic representation of a longitudinal cross-section of the embodiment of FIG. 1, taken along the line 2—2 of FIG. 1, illustrating the distribution of electric lines of force.

While the apparatus described may be adapted to maintain steady state ion concentration gradients of any desired ion in focusing channel 30a (through an appropriate selection of electrolyte 33 and membrane 34), the embodiment so far described is designed to provide a pH gradient in the range of 4.5 to 5 within focusing channel 30a. A qualitative understanding of the process for maintaining such a gradient may be gained through reference to FIG. 2. As the structure defining conduit 30 the chambers 31 and 32 is of electrically non-conductive material, the current flow through the conduit between cathode and anode is essentially by electrolytic conduction. Ideally, selectively permeable membrane 34, which partitions the electrolyte in conduit 30, is chosen to have a conductivity of the same order of magnitude as electrolytic solution 33, although this condition is not necessary. Assuming the conductivities of electrolyte and membrane to be the same for purposes of illustration, it can be shown (by the theory of electrically conducting media) that a steady state electric field within conduit 30 varies along the channel, decreasing in magnitude from position to position along the conduit as the cross-sectional area of the channel increases. This decrease in electric field can be visualised as an increase in the spacing between a set of electric lines of force 40. (For a discussion of the resolution of an electric field in an electrolyte into field lines, see G. P. Harnwell, "Principles of Electricity and Electromagnetism," McGraw Hill Publishing Company, New York, 1949.) As the external walls of conduit 30 are nonconducting, the total number of lines of force passing through any transverse cross-section of the conduit must remain constant for a given applied field. To the extent electrolytic solution 33 and membrane 34 are of the same conductivity throughout the conduit, the density of the lines of force is inversely proportional to the transverse cross-section of the conduit. As focusing channel 30a is of constant cross-section while ancillary channel 30b is variable, the lines of force 40 pass out of channel 30a and into the increasing volume of ancillary channel 30b. This is to say, there is a component of the electric field normal to membrane 34 such that lines of force 40 pass through the membrane. The electric lines of force 40 within focusing channel 30a become less dense on progressing from chamber 31 to chamber 32. Consequently, the component of electric field parallel to the longitudinal axis of focusing channel 30a decreases in magnitude in moving from anode to cathode along the channel.

Now consider focusing channel 30a to be composed of a set of small contiguous segments separated from each other by hypothetical transverse cross-sectional surfaces. Referring to FIG. 1, one such segment 41 is shown separated from neighboring segments by the hypothetical cross-sectional surfaces 42 and 43. As the cross-sectional area of ancillary channel 30b in the plane of hypothetical surface 43 is larger than that in the plane of hypothetical surface 42, the component of electric field parallel the longitudinal axis of focusing channel 30a (and hence normal to the hypothetical surfaces 42 and 43) is larger at hypothetical surface 42 than it is at hypothetical surface 43.

Under the influence of an electric field between anode and cathode, cations, such as the sodium ions of electrolytic solution 33 of the example, will move toward the cathode and anions, such as the acetate ions, will move toward the anode. With a selectively permeable membrane 34 that is anion selective, cations within channel 30a are confined to move along the channel. That is, the mobility of cations through such a membrane may be considered negligibly small, as an anion selective membrane is much less permeable to cations than it is to anions. With the acetic acid and sodium acetate electrolyte of the example, the flux of sodium ions into segment 41 therefore occurs only through hypothetical surface 42; similarly the flux of sodium ions out of segment 41 occurs only through hypothetical surface 43. Consideration of the theory of electrically conducting media and the theory of electrolytes leads to the conclusion that the flux of ions through a hypothetical surface due to electric forces is proportional to the component of electric field normal to the hypothetical surface, proportional to the hypothetical surface area, and proportional to the concentration of ions at the hypothetical surface. Thus, for an initial condition in which the ion concentration is everywhere the same, the flux of sodium ions into segment 41 through surface 42 will be greater than the flux of sodium ions out of segment 41 through surface 43. The concentration of sodium ions within segment 41 thus increases. However, with an increase in ion concentration in segment 41, the flux of sodium ions out of segment 41 through hypothetical surface 43 will also increase. Assuming the ion concentration at hypothetical surface 42 is held constant, the ion concentration of segment 41 will cease to increase when the flux of sodium ions out of segment 41 through hypothetical surface 43 is equal to the flux of sodium ions into segment 41 through hypothetical surface 42. Applying this argument to all of the small segments that comprise channel 30a, beginning with the small segment adjacent to aperture 35 at anode electrolyte chamber 31, and taking into account ion transport due to diffusion, it can be seen at least qualitatively how a steady state sodium ion concentration gradient may result.

Charge balance, i.e., the requirement that a volume element of an electrolyte may acquire no net electric charge, suggests that a corresponding acetate ion concentration gradient should also result. The concentration gradient of sodium acetate taken together with the essentially constant concentration of acetic acid (the acetic acid molecule is a neutral species) results in a pH gradient in the range, for example, of 4.5 to 5.

It will be appreciated that the above argument is a simplification of real physical phenomena. A more exact treatment would require taking into account other phenomena such as electroendosmosis and Donnan equilibria.

The above-described method for establishing an ion concentration gradient and in particular a pH gradient for use in isoelectric focusing has several advantages. First, the ion concentration gradient depends positionally upon the physical form of the device, e.g., referring to FIG. 1, the form of ancillary chanel 30b. Therefore this method is not subject to cathodic drift as is the prior art method. Additionally, ion concentration gradients may be obtained within a very narrow range of values, e.g., this may be accomplished by varying the cross-sectional area of ancillary channel 30b over a narrow range. Then again, the above described method does not require the use of carrier ampholytes and hence does not suffer from the untoward aspects associated therewith.

Figure 3:
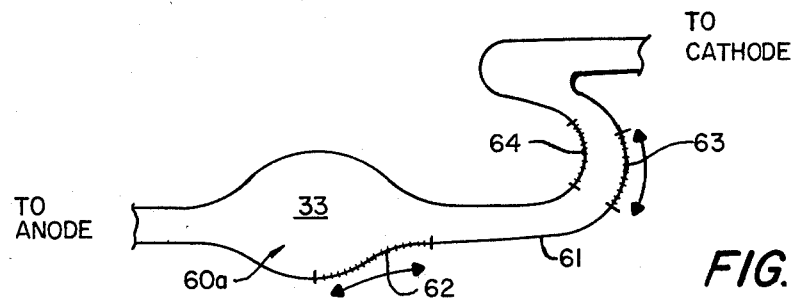
FIG. 3 is a fragmentary schematic representation of an alternative embodiment of the invention incorporating a channel of arbitrary shape.

A number of modifications may be made to the apparatus without departing from the scope of the invention. For instance, the channel in which the ion concentration gradient is established may be of arbitrary shape provided that at least a portion extending generally in a direction from anode to cathode of the bounding surface is constructed in such a way that electric field lines pass through this portion, resulting in a net change in the number of electric field lines along the focusing channel, and that such portion is also selectively permeable to the ions of the electrolyte. For example, focusing channel 60a may be of convoluted shape with variable cross-section as shown in FIG. 3. Channel 60a is defined by wall 61 which generally is of a material impermeable to electrolyte solution 33 and also non-conductive. Wall 61 may be formed of materials such as glass, acrylic, or the like, by any of a number of processes such as blowing or casting. Wall 61 is provided with a number of sections, 62, 63, and 64, in which the non-conductive impermeable material has been replaced by a selectively permeable material.

Figure 4:
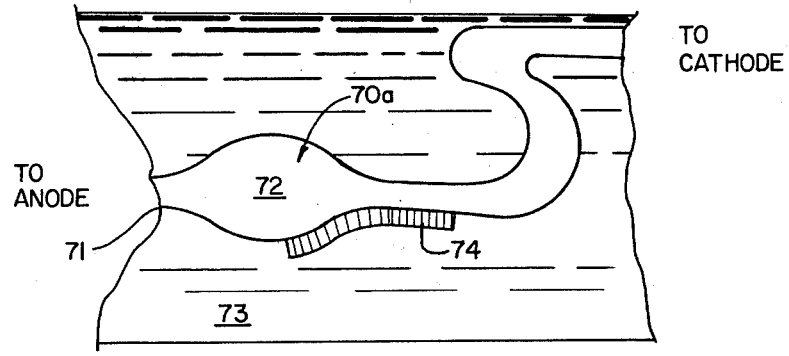
FIG. 4 is a fragmentary schematic representation of an embodiment similar to that of FIG. 3 and having a bounding surface portion comprising a selectively permeable membrane separating the electrolyte within the channel from an outside electrolytic medium.

More particularly the focusing channel may be of arbitrary shape and at least a portion of the channel wall extending generally in a direction from anode to cathode may comprise a surface of a selectively permeable membrane separating the electrolyte within the channel from an outside electrolyte. For example, referring to FIG. 4, focusing channel 70a may be in the form of a convoluted tube 71 of varying cross-section immersed in electrolyte. Generally tube 71 is impermeable and electrically non-conductive. Tube 71 encloses electrolyte 72 and is surrounded by electrolyte 73. Electrolytes 72 and 73 may have the same composition or they may be different. A portion of tube 71 is replaced with selectively permeable membrane 74. While internal electrolyte 72 communicates with anode and cathode means (not shown) along focusing channel 70a, external electrolyte 73 may communicate more directly with either or both, or with an auxiliary electrode. In this way, electric lines of force may be made to pass through membrane 74.

Figure 5:
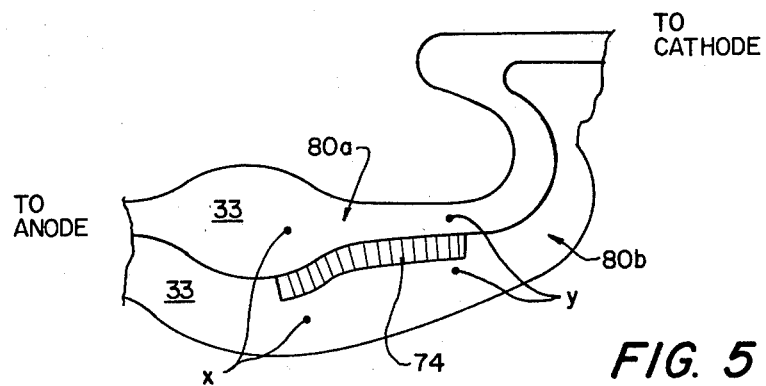
FIG. 5 is a fragmentary schematic representation of another embodiment incorporating a channel of arbitrary shape that has a bounding surface portion comprising a selectively permeable membrane separating the channel from an ancillary channel.

The outside electrolyte medium may be contained within an ancillary channel of regular shape or it too may be confined within an ancillary channel of arbitrary shape, such as channel 80b of the embodiment illustrated in FIG. 5. Both channels 80a and 80b communicate directly with the anode chamber and the cathode chamber, and, with the exception of membrane 74, common to both, are constructed in the form of hollow contiguous, impermeable electrically non-conductive tubes. Both channels may be of arbitrary shape and size provided that the ratios of their transverse cross-sectional areas between anode chamber and membrane 74 should differ from a similar ratio taken between membrane 74 and cathode chamber. That is, if the cross-sectional area of ancillary channel 80b is r at the general location between anode and membrane 74 denoted x in FIG. 5, and the cross-sectional area of channel 80a is s at a corresponding location, while at position y, between membrane and cathode, the cross-sectional area of ancillary channel 80b is p and the cross-sectional area of channel 80a is q, then r/p must be different from s/q.

Figure 6:
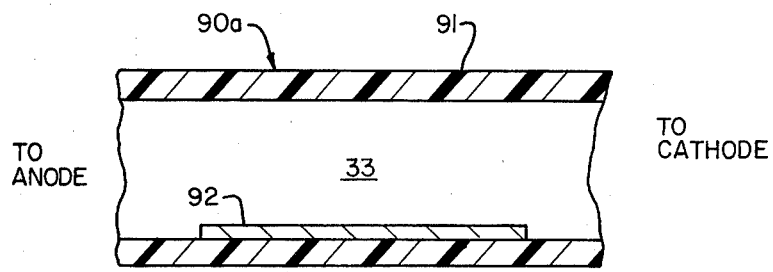
FIG. 6 is a fragmentary schematic representation of another embodiment in which a portion of the surfaces bounding the channel is an electrically conducting film.

In addition to providing a selectively permeable membrane separating a focusing channel from an ancillary channel as a means to effect a bounding surface through which electric lines of force pass various solid electrically conducting materials held at differing electrical potentials may be disposed as part of the walls of the channel or within the channel. Such electrodes may obviously serve as sources or sinks of the electric lines of force. Further, by supplying a source or sink of electrons, such electrodes may also serve as a source or sink of anions or cations. For example, referring to FIG. 6, focusing channel 90a, in the form of a glass tube 91 having an inner wall coated with a thin film 92 of a conducting material, such as platinum, graphite, or the like, may be seen. The film is preferably sufficiently thin so as to have a relatively high electrical resistivity. An electrical potential difference may then be applied between two spaced apart points on the film. Although film 92 is not selectively permeable to the ions of the electrolyte, an effect equivalent to having a selectively permeable membrane may occur, depending upon the electrolyte, since the electrode is a source (or sink) for electrons. Thus, if electrolyte 33 is a dilute solution of sulfuric acid, the availability of free electrons at film 92 would convert some of the hydronium ions of the electrolyte into atomic (non-ionized) hydrogen and oxygen, and a resulting sulphate gradient along the channel would occur.

Beyond serving as an ion source or sink by providing (or removing) electrons, film 92 might also serve such a function by reacting with constituents of the solution or by catalyzing such reactions. In such embodiments, both solution and film are chosen such that, on contact with the film, only selected ions of the solution react, the others remaining unchanged. Typical reactions useful in this respect react these ions to form a neutral solvent (or, more generally, gaseous) molecule, or form a radical or opposite electric charge. It will be appreciated that this method is inferior to the method utilizing a selectively permeable membrane principally because of the chemical modifications that may affect electrolyte, solvent, and amphoteric substances, and because of the usual evolution of gases that accompany this configuration.

Figure 7:
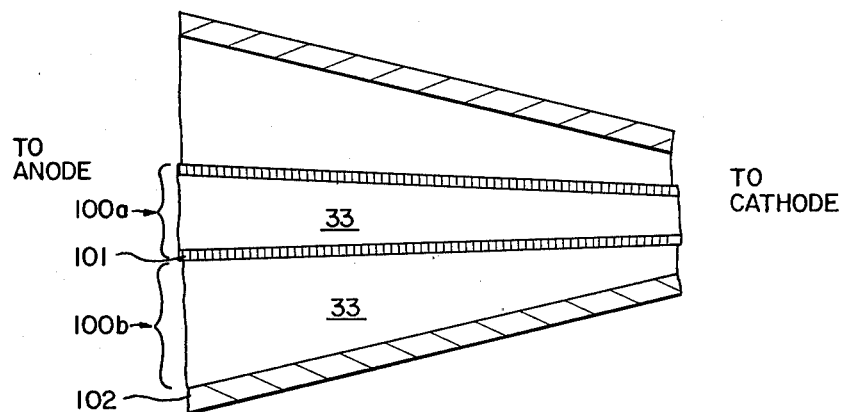
FIG. 7 is a fragmentary schematic representation of an alternative embodiment of the present invention employing a selectively permeable membrane in the form of a conical frustum.

As previously indicated, the wall of the focusing channel may have one or more regions which are ion-selective membranes. A particularly convenient configuration replaces the entire wall of the focusing channel with such a membrane. Referring to FIG. 7, there may be seen focusing channel 100a delimited by wall 101 in the form of an open-ended hollow conical frustum having an altitude substantially larger than the diameter of its larger base. Wall 101 may be formed from a planar sheet of selectively permeable membrane cut and folded to conform to the shape of the conical frustum. It will be appreciated that with this configuration the cross-sectional area of channel 101a varies from position to position. Ancillary channel 101b is provided with an outer wall 102 in the form of an open-ended conical frustum fabricated from an insulating material such as glass or acrylic plastic. Wall 102 is dimensioned such that the altitude of the frustum it forms is substantially equal to that of the frustum formed by wall 101, and so that its larger and smaller diameters are greater than the corresponding diameters of wall 101. Channel 101a is placed coaxially within channel 100b, with the respective larger and smaller diameter bases of the two frustums coplanar. It will be understood that walls 101 and 102 may be secured in such spaced-apart relationship by any of a number of means, such as a number of small radial struts (not shown). Ancillary channel 102 is thus bounded by walls 101 and 102, and is itself in the form of a thick hollow conic frustum of varying thickness. To insure that electric field lines pass through wall 101, the gradients of the cross-sectional areas of channels 100a and 100b are chosen to be different.

Channel 101 and ancillary channel 102 may each be provided with two entranceways to the anode and cathode electrolyte chambers, respectively. Alternatively, channel 101 may be provided with entranceways to anode and cathode electrolyte chambers while entranceways from ancillary channel 102 into anode and cathode electrolyte chambers respectively are blocked by planar sheets of insulating material such as glass or acrylic plastic.

Figure 8:
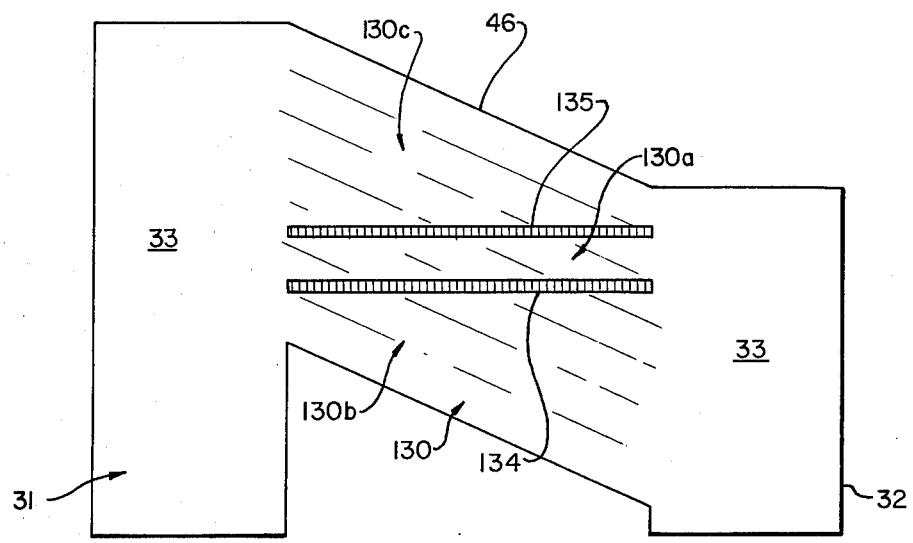
FIG. 8 is a schematic representation of a longitudinal cross-section of an alternative embodiment of the present invention incorporating a pair of ancillary channels.

Another particular modification may provide a focusing channel with two ancillary channels containing electrolyte. Referring to FIG. 8, there may be seen a conduit 130 of uniform rectangular section communicating between anode and cathode chambers 31 and 32 respectively. Disposed obliquely within conduit 130 is focusing channel 130a, also of uniform rectangular section. Focusing channel 130a is bounded top and bottom respectively by membranes 135 and 134. In general, both membranes 134 and 135 may be selectively permeable membranes, provided that they are not identical with respect to their selective permeability. Thus, membrane 135 may be an ultrafiltration membrane that is permeable to all of the ions of the electrolyte but impermeable to the amphoteric substances to be subjected to isoelectric focusing, while membrane 134 may be an anion selective membrane. The oblique disposition of focusing channel 130a defines a pair of oppositely tapering ancillary channels, 130b and 130c. As shown in FIG. 8 the transverse cross-sectional area of the first ancillary channel 130b increases from anode to cathode, whereas the transverse cross-sectional area of the second ancillary channel 130c increases from cathode to anode. Membranes 134 and 135 are bound to the walls of conduit 130 such that focusing channel 130a may communicate with ancillary channel 130b only through membrane 134 and with ancillary channel 130c only through membrane 135. Electric lines of force 140, of uniform density throughout conduit 130, are shown passing through focusing channel 130a through membranes 134 and 135 such that there is a component of electric field parallel to the longitudinal axis of focusing channel 130a as well as a component normal to the bounding surfaces formed by membranes 134 and 135. In all other respects, the embodiment shown in FIG. 8 may be the same as that shown in FIGS. 1 and 2.

Yet other variations of the invention are possible. With an additional modification, ancillary channel 130b of FIGS. 1 and 2 may be provided with a continuous flow of an electrolyte solution having fixed ionic concentrations. For example, channel 30b could be a part of the recirculating system joining anode and cathode chambers 31 and 32. This continuous flow taken together with the sheet form of channel 30b, makes it particularly simple to cool focusing channel 30a with, say, a cold water heat exchanger adjacent channel 30b. Alternatively, or additionally, the electrolyte solution flowing through ancillary channel 30b may be cooled prior to entering the ancillary channel.

It will also be appreciated that various combinations of electrolytes and selectively permeable membranes may result in a large variety of ion concentration gradients. For example, pH buffer ions of weak acids together with conjugate bases well known in the art of formulating pH buffer solutions may be used. Among these are, for instance, potassium dihydrogen phosphate ($KH_2PO_4$) together with disodium hydrogen phosphate ($Na_2HPO_4$) in a solvent such as water of dimethylsulfoxide (DMSO); tris(hydroxymethyl)aminomethane ($C_4H_{11}NO_3$) with HCl; and imidazole ($C_3H_4N_2$) together with hydrogen chloride (HCl). Dilute solutions of strong acids or strong bases, such as hydrogen chloride or sodium hydroxide in water may also be used. In addition, one may use solutions of salts such as sodium chloride or ammonium sulfate in water. Further, combinations of the components cited above may also be used. Any of these electrolytes may be used with either anion or cation selective membranes. The cation selective membrane may be formed, for example, from a cation membrane sheet such as that manufactured by Ionics, Inc., of Watertown, Mass. as sheet number 61-AZL-386. Other membranes in addition to anion and cation selective membranes may be used; e.g., various ultrafiltration and dialysis membranes may be used that are selective with respect to molecular size or shape. Furthermore, different selectively permeable membranes may be used at different locations along the same focusing channel. Thus, for instance, the focusing channel may be provided with an anion selective membrane in one area and a cation selective membrane in another.

It will also be understood that the direction in which the ion concentration increases, either increasing in the direction of the cathode or increasing in the direction of the anode, may be reversed by reversing the direction in which the transverse cross-sectional area of the ancillary channel increases. That is, if the direction in which the cross-sectional area of the ancillary channel increases is reversed, the direction in which the magnitude of the electric field increases in the channel will also be reversed. This will result in the reversal of the ion concentration gradient.

While a particular advantage of the present invention is in that it does not require anti-convective media within the focusing channel, such media may be used if desired. Thus, known anti-convective media as silica gel or polyacrylamide gel may be used to fill the focusing channel. The present method is also adaptable to the process of "continuous flow" isoelectric focusing. (For a further discussion of this process, see John S. Fawcett, Annals of the New York Academy of Sciences, volume 209, 1973, p. 112, and P. G. Righetti and E. Gianazza, Journal of Chromatography, volume 184, 1980, p. 415.) With the preferred embodiment shown in FIG. 1, a slow continuous flow of electrolyte solution may be introduced into focusing channel 30a through suitable input and output ports. This flow may occur generally in a direction parallel to selectively permeable membrane 34, but perpendicular to the direction from anode to cathode. Additionally, very rapid separations may be performed by applying a high voltage between anode and cathode with or without anti-convective media within the isoelectric focusing channel.

Finally, it should be noted that in the preferred embodiment as shown in FIG. 1, the selectively permeable membrane 34 also may serve to retain within channel 30a the amphoteric molecules to be separated. If selectively permeable membrane 34 is insufficient for this purpose, or if it is necessary to prevent the molecules or other particles to be separated from coming into contact with the selectively permeable membrane, suitable means such as, for example, an ultrafiltration membrane may be superimposed over the selectively permeable membrane.

Since these and other changes may be made in the above method and apparatus without departing from the scope of the invention herein involved, it is intended that all matter contained in the above description or shown in the accompanying drawings shall be interpreted in an illustrative and not in a limiting sense.

What is claimed is:

1. An apparatus for establishing an ion concentration gradient in an electrolyte containing two or more types of ions, said apparatus comprising, in combination:
   a channel defined by at least one bounding surface suitable for containing said electrolyte; and
   anode means and cathode means disposed in fluid communication with said electrolyte for establishing an electric field within electrolyte contained in said channel;
   wherein at least a portion of said bounding surface is selectively permeable to the ions of said electrolyte contained in said channel, and is disposed and constructed such that electric lines of force of said electric field pass therethrough while a substantial component of said field is parallel to said bounding surface.

2. An apparatus for establishing an ion concentration gradient in an electrolyte containing two or more types of ions, said apparatus comprising, in combination:
   an elongate conduit for containing said electrolyte;
   anode means and cathode means disposed in fluid communication with said electrolyte for establishing an electric field within electrolyte contained in said conduit; and
   wall means extending from said anode means to said cathode means and bifurcating said conduit so as to form a focusing channel and an ancillary channel, at least a portion of said wall means being selectively permeable to a one of said types of ions of said electrolyte, said portion having a conductivity of the order of magnitude of said electrolyte;
   wherein said conduit and said wall means are configured and disposed such that a portion of said electric field will extend between said focusing channel and said ancillary channel through said portion.

3. Apparatus according to claim 1 or 2 wherein said portion comprises a selectively permeable membrane.

4. Apparatus according to claim 3 wherein said selectively permeable membrane is an anion selective membrane.

5. Apparatus according to claim 3 wherein said selectively permeable membrane is a cation selective membrane.

6. Apparatus according to claim 2 wherein said elongate conduit is of varying transverse cross-section and wherein said wall means is disposed such that a one of said pair of channels is of substantially constant cross-section.

7. Apparatus according to claim 2 wherein said portion is a selectively permeable membrane comprising substantially all of said wall means and wherein said focusing channel and said selectively permeable membrane are in the form of thin sheets.

8. An apparatus for establishing an ion concentration gradient in an electrolyte containing two or more types of ions, said apparatus comprising, in combination:
   a channel defined by at least two bounding surfaces suitable for containing said electrolyte;
   anode means and cathode means disposed of and in fluid communication with said electrolyte for establishing an electric field within electrolyte contained in said channel;
   wherein at least a portion of said at least one bounding surface is a source or sink of selected ions of said electrolyte disposed and constructed such that electric lines of force of said electric field pass therethrough while a substantial component of said electric field is parallel said bounding surface.

9. A process for establishing an ion concentration gradient in an electrolyte solution comprising the steps of:
   confining said electrolytic solution in a channel defined by a bounding surface a portion of which is selectively permeable to at least one of the ions of said solution; and
   establishing an electric current through said solution such that a substantial portion of the electric lines of force of said current have components parallel to said portion and at least some of said lines of force pass through said portion.

10. A process for establishing an ion concentration gradient in an electrolyte solution comprising the steps of:
    dividing said electrolytic solution by a partition which includes a portion selectively permeable to at least one of the ions of said solution; and
    establishing an electric current through said solution such that a substantial portion of the electric lines of force of said current having components parallel to said portion and at least some of said lines of force pass through said portion.

11. A process for separating a mixture of amphoteric particles having differing isoelectric points comprising the steps of:
    confining an electrolytic solution in a channel defined by a bounding surface a portion of which is selectively permeable to at least one of the ions of said solution;
    establishing an electric current through said solution such that a substantial portion of the electric lines of force of said current have components parallel to said portion and at least some of said lines of force pass through said portion; and
    introducing said mixture of amphoteric particles into said electrolyte.

12. A process of separating a mixture of amphoteric particles having differing isoelectric points comprising the steps of:
    dividing an electrolytic solution by a partition which includes a portion selectively permeable to at least one of the ions of said solution;
    establishing an electric current through said solution such that a substantial portion of the electric lines of force of said current have components parallel to said portion and at least some of said lines of force pass through said portion; and
    introducing said mixture of amphoteric particles into said electrolyte.

* * * * *

UNITED STATES PATENT AND TRADEMARK OFFICE
CERTIFICATE OF CORRECTION

PATENT NO. : 4,401,538
DATED : August 30, 1983
INVENTOR(S) : A. David Hausfeld

It is certified that error appears in the above-identified patent and that said Letters Patent is hereby corrected as shown below:

Claim 8, column 14, line 1, please delete "two" and substitute therefore -- one --; and Claim 8, column 14, line 1, please delete "surfaces" and substitute therefore -- surface --.

Signed and Sealed this

Eighth Day of November 1983

[SEAL]

Attest:

GERALD J. MOSSINGHOFF

Attesting Officer

Commissioner of Patents and Trademarks